United States Patent [19]

Michl et al.

[11] 4,281,991

[45] * Aug. 4, 1981

[54] DENTAL PROSTHESES

[75] Inventors: Rudy Michl; Peter Wollwage, both of Mauren, Steinbos, Liechtenstein

[73] Assignee: Perdent, GmbH, Schaan, Liechtenstein

[*] Notice: The portion of the term of this patent subsequent to May 21, 1998, has been disclaimed.

[21] Appl. No.: 926,398

[22] Filed: Jul. 20, 1978

Related U.S. Application Data

[62] Division of Ser. No. 543,532, Jan. 23, 1975.

[30] Foreign Application Priority Data

Jan. 23, 1974 [DE] Fed. Rep. of Germany ....... 2403211

[51] Int. Cl.$^3$ .................................................. A61K 6/08
[52] U.S. Cl. .................................. 433/202; 260/42.15; 260/42.52; 260/42.49; 260/998.11; 264/16; 264/19; 433/212
[58] Field of Search ............. 260/42.52, 998.11, 42.15, 260/42.49; 433/202, 212; 264/16, 19

[56] References Cited

U.S. PATENT DOCUMENTS

| | | | |
|---|---|---|---|
| 2,874,140 | 2/1959 | Kloepfer | 260/42.52 |
| 4,029,632 | 6/1977 | Gross et al. | 260/998.11 |

OTHER PUBLICATIONS

Lee et al., Epoxy Resin Dental Materials, May 1967, National Institute of Health and National Institute of Dental Research, RR 67-112.

Hirasawa et al., Physical Properties as Dental Materials of Polymethyl Methacrylates Mixed with Silica Gel, Reports of the Institute for Medical and Dental Engineering, 2.55–61, 1968.

*Primary Examiner*—James H. Derrington
*Attorney, Agent, or Firm*—Fidelman, Wolffe & Waldron

[57] ABSTRACT

Dental prosthetic devices, such as artificial teeth, crowns, bridges and replacements for parts of teeth are provided comprising hardened resin dental materials containing at least one polymer and a finely divided inorganic filler, said filler being present in an amount of about 10 to 90% based on the weight of the material and having a particle size within the range of 10 to 400 millimicrons, said materials having an extremely high compressive strength, clear opalescence and a very smooth homogeneous surface.

17 Claims, No Drawings

DENTAL PROSTHESES

This is a divisional of application Ser. No. 543,532, filed Jan. 23, 1975.

The present invention relates to materials for dental purposes which contain at least one polymerizable monomer and/or polymer which is suitable for dental purposes and a finely divided filler.

By the expression "material for dental purposes" there are meant for instance fillings for cavities, fastening cements, sealing and protective coatings, crown and bridge materials, prosthesis materials as well as compositions for the production of artificial teeth having a base of polymerizable monomers and/or polymers.

Monomers or polymers which are suitable for dental purposes comprise for instance polyvinyl chloride, polystyrene and their copolymers, polyamides, epoxy compounds, polyurethanes and, in particular, monomeric and polymeric acrylates and methacrylates (see Ullmanns Enzyklopadie der Technischen Chemie, Volume 5, 1954, pages 717 to 721).

In the manufacture of artificial teeth or parts of teeth one customarily starts with polymethacrylates in the form of bead or chip polymers which can normally be processed in molds by heating with the addition of the corresponding monomers. Mixtures of monomeric and polymeric methacrylates are used for instance as prosthesis, crown, and bridge material, the monomer contained in the mixture being fully polymerized in the presence of the polymer. Monomers alone are customarily used as fastening cements and sealing and protective coatings and recently also as filling material.

In the following description reference is had primarily to prosthesis material and filling material since special problems arise in connection with these materials. A considerable shrinkage occurs upon the polymerization of the monomeric acrylates or methacrylates customarily used. For this reason since a very early stage a paste or bead polymer and monomer in a weight ratio of 2:1 has been used for the production of prosthesis material. To be sure, the contraction is still then 7%. In addition to this there is a high linear coefficient of thermal expansion (TK) of $81.0 \times 10^{-6}$ mm/mm° C. As compared with this the coefficient of thermal linear expansion (TK) of the natural tooth is only about $\frac{1}{8}$, i.e. $11.4 \times 10^{-6}$.

An increase in use for tooth fillings and similar purposes occurred first of all by the use of the long-chain monomers having a base of bisphenol A and glycidyl-methacrylate in accordance with U.S. Pat. No. 3,066,112. These new monomers, generally known as Bis-GMA, have less shrinkage. In order still further to reduce the shrinkage these monomers are futhermore mixed with about three times their quantity of inert inorganic fillers. They therefore consist of about 25% of a cold polymerizable monomer mixture as binder and about 75% inorganic fillers, preferably the oxides of aluminum and silicon or else silicate glasses, calcium carbonate in various forms, such as beads, fibers, etc.

In this way not only is the above mentioned polymerization contraction reduced to an amount suitable for the purpose of use, i.e. about 1%, but the TK (coefficient of linear thermal expansion) is also reduced to about $20-30 \times 10^{-6}$ mm/mm/°C.

Instead of the aforementioned monomer Bis-GMA the binder mixture may also contain other derivatives of Bisphenol-A or else urethane derivatives produced by addition, for instance derivatives of diisocyanates and hydroxyalkylmethacrylates. In general, up to 15% short-chain methacrylates and/or also the known cross linking agents such as for instance triethyleneglycoldimethacrylate are added in order to reduce the viscosity.

For fillings two pastes are generally mixed together, each containing binder and filler. The Redox system used for the catalysis of the polymerization is distributed in the manner that one paste contains only the peroxide catalyst while the other contains the amine initiator.

The inorganic filler is "silanized" before mixing in order to obtain a better bonding to the organic matrix, i.e. it is coated with suitable unsaturated silane compounds. The materials referred to as composite materials are used with a filler content adapted to the purpose of use not only for fillings in cavities of the front teeth but also as fastening cements, for the sealing of cracks and for caries prophylaxis as protective coatings for teeth as well as for crown and bridge material.

It has now been found that while having in general rather good mechanical properties these materials are very difficult to polish and futhermore very frequently have insufficient transparence. It has been attempted to improve the polishability by using finely divided inorganic fillers whose particles should have at most a diameter of about 30$\mu$ (see German Unexamined Application for Patent No. 2 126 419). Unfortunately the transparency was impaired upon the reduction in the particle size. The surface which was already inhomogeneous to start with became rough due to uneven abrasion after some time and therefore offered the opportunity for discloration.

Even when the particle size of the inorganic filler particles was reduced to a minimum size of 0.8 to 8$\mu$ and a maximum size of about 3 to 20$\mu$ (see German Unexamined Application for Patent No. 2 312 258), the polishability and in particular the transparency of the both fillings were still unsatisfactory.

It is furthermore known from German Provisional Patent No. 1 928 831 and German Unexamined Applications for Patent Nos. 2 126 419, 2 164 668 and 2 224 683 further to add silica, in a particle size of less than 1$\mu$ and in quantities up to 8% by weight referred to the total weight, to the tooth filling compositions in addition to the customary inorganic fillers. This addition however is merely for the purpose of thickening the monomer in order to prevent the sedimentation of the larger particles of filler. In German Unexamined Application for Patent No. 2 164 668 it is stated that particles which are smaller than 0.7$\mu$ must be removed by suitable methods since otherwise the transparency of the filler is excessively impaired. Also in German Unexamined Application for Patent No. 2 126 419 it is stated that the silica used as thickening agent and having a particle size of 50 to 2000 Å should be added only in a very small percentage of about 5 to 8% by weight, referred to the total composition.

The disadvantages mentioned in said literature in connection with the use of silica of a particle size of less than 1$\mu$ were possibly due to the fact that it was used together with larger quantities of a filler having a larger particle size.

It has namely surprisingly been found that an improvement both in the mechanical properties and in the polishability is possible without impairing the transparency of the materials used for dental purposes by using, as inorganic filler, a filler having a particle size of less than about 400 m$\mu$.

The object of the present invention is thus a material for dental purposes of the above-indicated type which is characterized by the fact that the micro-fine inorganic filler present in an amount of about 10 to 90% (referred to the weight of the material) has a particle size of less than about 400 m$\mu$.

In accordance with a particularly preferred embodiment, at least 50% of the micro-fine inorganic filler particles have a particle size within the range of about 10 to 40 m$\mu$.

The micro-fine inorganic filler results in a thickening of the monomer and imparts thixotropic properties to the material so that this mixture can be liquefied again by simple stirring.

Upon the use of more highly viscous monomers or of monomer-polymer mixtures, the micro-fine inorganic filler is advisedly added in smaller quanitites within the above indicated range so that the mixture does not become too viscous. However, the percentage of the micro-fine inorganic filler can be increased even in the case of monomers or mixtures having a higher initial viscosity if one selects a filler whose BET surface area is less than about 200 m$^2$/g. The BET surface area of such a filler is preferably between about 30 and 80 m$^2$/g.

The quantity of micro-fine inorganic filler preferally is within the range of about 20 to 80% and preferably within the range of 40 to 75%, referred to the total total weight of the material. The most favorable ranges, as mentioned above, depend inter alia on the BET surface area of the filler and on the viscosity of the polymerizable monomer and/or polymer.

The micro-fine inorganic filler preferably consists of silica* or alumina. Furthermore** silicate glasses and similar fillers can also be used provided that their particle size is less than 400 m$\mu$.

*and/or
**in the sense of in addition

The micro-fine inorganic filler can be "silanized". For this purpose it is customarily treated with a silane which bears polymerizable organic groups on the silicon atom. The polymerizable groups react with the polymerizable monomer of the organic components, whereby a good bond is obtained between the organic component and the inorganic filler. With the micro-fine inorganic fillers used in accordance with the invention a silanizing however is not absolutely necessary, in contradistinction to the coarse fillers used heretofore.

By the use of the micro-fine inorganic filler, there are obtained dental materials and particularly filling materials, having an extremely high compressive strength, excellent transparency and a very smooth homogeneous surface. The difference in the nature of the surface between a commercial filling material and a filling material which contains the micro-fine inorganic filler can be noted even with the naked eye. The difference can be seen even more clearly under a microscope. While no individual particles can be noted any longer in the case of the filler material which contains the micro-fine filler (the surface appears as a homogeneous unit) the individual particles can clearly be noted in chip or bead shape in the case of the commercial filler material. With the micro-fine filler it is possible to overcome the previously existing contradiction with respect to the requirements of high transparency and good polishability. Furthermore, the dental materials of the invention exhibit opalescence. This means an important improvement in the cosmetic effect since the layer of plastic appears yellowish in transmitted light and bluish-white in incident light, as is also true of natural teeth. The materials of the invention are therefore particularly well suited as filling for front teeth.

The above mentioned Bis-GMA can be used for instance as monomer for such filling compositions. However, other derivatives of Bisphenol-A or else the reaction products of hydroxyalkylmethacrylates and isocyanates can also be used. These monomers generally have a relatively high viscosity so that in general short-chain monomeric methacrylates are also added in order to reduce the viscosity. Difunctional esters of acrylic or methacrylic acid can be added as cross-linking agents. The micro-fine filler serves as inorganic filler.

If the micro-fine filler is used to improve the properties of dental materials which are to be polymerized at room or mouth temperature (autopolymers), the kedox catalyst system which supplies free radicals and is customary for cold polymerization must, of course, be used. It consists of organic peroxide catalysts, preferably benzoylperoxide, and activators, preferably tertiary amines.

Therefore it is possible in this way to produce a so-called composite material for fillings and other purposes which consists of two separately stored components A and B which are preferably in paste form. Both of them contain organic binder system and filler, and in addition one of the two components contains the catalyst and the other activator. Depending upon the purpose of use the amount of inorganic filler to be added varies. In the case of a composite material for filling purposes it can, for instance, amount to 60 to 65% while the organic matrix consists of 20 to 22% Bis-GMA and 15 to 18% ethyleneglycol dimethylacrylate.

The organic binder mixture is intimately mixed with the micro-fine inorganic filler until a paste substance is obtained. 0.5 to 2% benzoylperoxide is subsequently added to the first component and 0.5 to 1% dimethyl-paratoluidine to the second paste.

In order to prepare a test specimen approximately equal parts of pastes A and B are taken and mixed on a mixing block, for which, in contradistinction to normal filling materials, a metal spatula can also be used. The working time of the material is about 2 minutes; within 5 minutes, the mixture has polymerized into a solid test specimen. The compressive strength measurements depending on the proportion of micro-fine filler used and varying the organic matrix give values of between 4000 and 6000 kg/cm$^2$ and are even superior to those of amalgam.

The bending strength reaches values of between 11 and 16 kg/cm$^2$; the water absorption at the end of two months is between 0.5 and 1.5%. The surface quality of a commercial filler material and of the filler material prepared in the above indicated manner is compared under a microscope after both surfaces have been polished to a high gloss by the customary techniques. It is found in this connection that the filler material containing the micro-fine filler used in accordance with the invention has a homogeneous, completely pore-free surface while in the commercial filler material the individual chip-shaped or bead-shaped particles can be seen imbedded in the matrix. Another surprising effect is that the new filling material exhibits opalescence, i.e. appears yellowish in transmitted light but bluish-white in incident light and thus substantially agrees with the optical properties of the natural tooth enamel, which is greatly desired, particularly for fillings in the region of the front teeth.

The micro-fine filler used in accordance with the invention can also serve to produce a substantially improved material for crowns, inlays and bridges. For this purpose, for instance, a crystalline dimethacrylate of a modified bisphenol-A is dissolved in an organic solvent, for instance chloroform or ether, and the micro-fine filler is added to the solution with constant stirring. In this way a paste is obtained which is then kneaded until the solvent has evaporated completely. The powder is ground in a ball mill and benzoylperoxide, for instance, is added as catalyst. After the mixture has been screened there is obtained a material for the production of crowns and bridges.

A crown is modeled, for instance, by heating the powder prepared in the above indicated manner in a porcelain dish to above the melting point of the crystalline monomer until there is obtained a thinly liquid slurry which can be worked with a brush or spatula. If it is applied in layers onto an insulated model stump and polymerized layer by layer, for instance in a stream of hot air, one obtains a tooth crown of excellent transparency and extreme resistance to abrasion. However, the crown may also be laminated in a cell in the customary manner from a polymer/monomer paste to which a corresponding quantity of micro-fine filler has been added and then polymerized by heating on a water bath.

It is furthermore possible to admix mechanically a polymethylmethacrylate in bead form to the micro-fine filler and plymerize the paste obtained by the addition of monomer at elevated temperature, for instance 100° C. under pressure in a metal mold to form a tooth or a facing shell.

A tooth produced in this manner had a very good opalescence, excellent physical properties such as compressive strength or bending strength and was clearly superior to traditional materials.

A particularly homogeneous distribution of the micro-fine filler in the polymer is obtained by preparing a paste from monomeric methylmethacrylate and the micro-fine filler, polymerizing it into a block under pressure and temperature and then crushing the block into a chip polymer. The polymer thus obtained is enriched with filler and can be used in ordinary fashion for the production of plastic teeth, tooth parts or as base material for prostheses.

In general, by the use of the micro-fine filler of the invention one obtains improved dental materials which are characterized by a substantially higher compressive strength, good polishability, excellent transparency together with low abrasion and which in their opalescence substantially agree with the appearance of th natural tooth enamel.

The examples given below will serve to assure a better understanding of the invention.

EXAMPLE 1

61.5 g of silica (average particle size between 10 and 20 mµ with a BET surface area of 50 m$^2$/g) are silanized in the customary manner with methacryloxy-propyl-trimethoxy silane and poured into a laboratory kneader. 22 g of Bis-GMA and 16.5 g of ethyleneglycol-dimethacrylate are added thereto and the kneading is continued until a homogeneous paste which is free of specks is obtained. 40 g of this paste are treated with 0.6 g of 50% benzoylperoxide (paste A). A further 40 g of the master paste are treated with 0.1 g of dimethylparatoluidine (paste B).

If equal quantities of paste A and B are mixed on a mixing block a filling material for dental cavities is obtained. The working time is 2 minutes; by 5 minutes the material is hard. A test specimen is produced in the manner described and stored in water of 37° C. for 24 hours.

The test body described above and a comparison body prepared from a commercial composite material for tooth fillings (with about 75% SiO$_2$, average particle size 30µ) are polished with a rubber polisher for 5 minutes. The surfaces of the two bodies are observed carefully under a microscope. The section of the material which contains the micro-fine silica shows a homogeneous uniformly smooth porefree surface while the commercial material still clearly shows the individual particles distributed in the matrix.

A few comparative values are given in the following table.

|  | Commercial filling material | Filling material of the invention |
|---|---|---|
| Compressive strength after 24 hours in H$_2$O, 37° C.(kg/cm$^2$) | 2700 | 4700 |
| Bending strength (kg/cm$^2$) | 11.0 | 11.7 |
| Water absorption at the end of 1 month (%) | 1.0 | 1.4 |
| Transparency at the end of 24 hours in H$_2$O, 37° C. (%) | 32 | 80 |

EXAMPLE 2

20 g of 2,2-Bis [4-(2-hydroxy-ethyoxy)-phenyl]-propane dimethacrylate are dissolved in 50 g of chloroform. 21 g of silanized silica having an average particle size of 30 mµ and a BET surface area of less than 80 m$^2$/g are added to this solution. The paste thus formed is dried with constant stirring until the crystalline monomer is again solid and the solvent has evaporated. In this way the silica is distributed completely homogeneously in the monomer. 0.5% benzoylperoxide is distributed in the powder by grinding it in a ball mill and thereupon screening it. This mixture is stable as long as it is not heated to above 42° C. For processing the powder is melted in a porcelain dish at 50°–60° C. and applied by a brush or spatula to an insulated model stump, it being polymerized layer in a stream of hot air at about 150° C. The crown obtained in this way is compared with a crown which has been prepared from a commerical material.

The crown with the micro-fine filler has opalescence, i.e. it looks bluish-white in incident light and therefore comes very close in cosmetic effect to natural tooth enamel. If both crowns are tested by brushing the crowns with precipitated chalk and a toothbrush the polymer containing the micro-fine silica is clearly more resistant to abrasion. A few comparative values will show the difference.

|  | Crown Containing micro-fine Silica | Crown prepared from a commercial material |
|---|---|---|
| Compressive strength kg/cm$^2$ | 3300 | 1360 |
| Bending strength kg/cm$^2$ | 11.5 | 6.0 |
| Ball indentation hardness kg/cm$^2$ | 2320 | 1600 |
| Water absorption at the end of |  |  |

|  | Crown Containing micro-fine Silica | Crown prepared from a commercial material |
|---|---|---|
| one month % | 0.8 | 1 |

EXAMPLE 3

100 g of the micro-fine filler used in Example 1 but which was not silanized are mixed with 30 g of uncolored polymethylmethacrylate present in the form of bead polymer as well as 2 g of 50% benzoylperoxide. A monomer mixture is prepared consisting of 35 g of monomeric methylmethacrylate and 35 g of a reaction product of hydroxyethyl-dimethacrylate and hexamethylene-diisocyanate. The powder and the liquid are mechanically mixed in a closed container on a swing mixing device until a viscous paste is obtained. This paste is introduced into a tooth mold and polymerized for 4 minutes at 110° C. The artificial tooth thus obtained shows clear opalescence, i.e. it appears yellowish in transmitted light and of a blue-while transparency in incident light. The ball indentation hardness is 2800 kg/cm$^2$ as compared with 1400 kg/cm$^2$ in the case of comparison teeth compared on basis of the customary methacrylate. The resistance of the plastic tooth containing the micro-fine filler to monomer, chloroform or boling water is definitely better.

What is claimed:

1. A dental prosthesis having clear opalescence, resistance to abrasion and capable of being polished, comprising a hardened composition, comprising:
    a first component comprising a monomeric binding material selected from a member of the group consisting of (a) long chain monomer esters of bisphenol A and glycidyl methacrylates, (b) adducts of diisocyanates and hydroxymethylacrylates, (c) difunctional esters of acrylic and methacrylic acids, and (d) mixtures of two, or of three of (a), (b) and (c), and
    a second component comprising a micro-fine inorganic filler being present in an amount of about 50 to 90% based on the weight of said composition and having a particle size within the range of about 10 to 400 millimicrons and a BET surface area of less than about 200 m$^2$/g, wherein at least 50% of the filler particles have a particle size within the range of 10 to 40 millimicrons, in admixture with at least one bead or chip polymer of the group consisting of polyvinylchloride and copolymers thereof, polystyrene and copolymers thereof, polyamides, polymeric acrylates and polymeric methacrylates.

2. The dental prosthesis according to claim 1, wherein the filler of the second component is present in an amount of 50 to 75% based on the weight of the composition.

3. The dental prosthesis according to claim 1, characterized by the fact that the micro-fine inorganic filler is a member selected from the group consisting of silicon-dioxide, aluminum oxide and silicate glass.

4. The dental prosthesis according to claim 3, characterized by the fact that the micro-fine inorganic filler is silanized before mixing with said polymer.

5. The dental prosthesis according to claim 1, wherein the monomeric binding material is selected from a member of the group consisting of long chain monomer esters of bisphenol A and glycidyl methacrylates.

6. The dental prosthesis according to claim 1, wherein the monomeric binding material is selected from a member of the group consisting of adducts of diisocyanates and hydroxymethylacrylates.

7. The dental prosthesis according to claim 1, wherein the monomeric binding material is selected from a member of the group consisting of difunctional esters of acrylic and methacrylic acids.

8. The dental prosthesis according to claim 1, wherein the polymer comprises a polymethylmethacrylate.

9. The dental prosthesis according to claim 1, wherein the surface area is between 30 and 80 m$^2$/g.

10. A method of making a dental prosthesis, comprising:
    a. forming a composition comprising:
        a first component comprising a monomeric binding material selected from a member of the group consisting of (a) long chain monomer esters of bisphenol A and glycidyl methacrylates, (b) adducts of diisocyanates and hydroxymethylacrylates, (c) difunctional esters of acrylic and methacrylic acids, and (d) mixtures of two, or of three of (a), (b) and (c), and
        a second component comprising a micro-fine inorganic filler being present in an amount of about 50 to 90% based on the weight of said composition and having a particle size within the range of about 10 to 400 millimicrons and a BET surface area of less than about 200 m$^2$/g, wherein at least 50% of the filler particles have a particle size within the range of 10 to 40 millimicrons, in admixture with at least one bead or chip polymer of the group consisting of polyvinyl chloride and copolymers thereof, polystyrene and copolymers thereof, polyamides, polymeric acrylates and polymeric methacrylates,
    b. molding said composition into an appropriate shape for making said dental prosthesis, and
    c. polymerizing said molded composition.

11. The method according to claim 10, wherein the filler of the second component is present in an amount of 50 to 75% based on the weight of the composition.

12. The method according to claim 10, characterized by the fact that the micro-fine inorganic filler is a member selected from the group consisting of silicon dioxide, aluminum oxide and silicate glass.

13. The method according to claim 12, characterized by the fact that the micro-fine inorganic filler is silanized before mixing with said polymer.

14. The method according to claim 10, wherein the monomeric binding material is selected from a member of the group consisting of long chain monomer esters of bisphenol A and glycidyl methacrylates.

15. The method according to claim 10, wherein the monomeric binding material is selected from a member of the group consisting of adducts of diisocyanates and hydroxymethylacrylates.

16. The method according to claim 10, wherein the monomeric binding material is selected from a member of the group consisting of difunctional esters of acrylic and methacrylic acids.

17. The method according to claim 10, wherein the polymer comprises a polymethylmethacrylate.

* * * * *